(12) United States Patent
Sugiura et al.

(10) Patent No.: US 8,030,429 B2
(45) Date of Patent: Oct. 4, 2011

(54) CATALYST FOR DEALCOHOLIZATION CONDENSATION REACTION AND METHOD FOR PRODUCING ORGANOPOLYSILOXANE USING THE SAME

(75) Inventors: Yasushi Sugiura, Chiba (JP); Masanori Sakai, Chiba (JP)

(73) Assignee: Dow Corning Toray Company, Ltd., Chiyoda-ku, Tokyo (JP)

( * ) Notice: Subject to any disclaimer, the term of this patent is extended or adjusted under 35 U.S.C. 154(b) by 54 days.

(21) Appl. No.: 12/521,057

(22) PCT Filed: Dec. 27, 2007

(86) PCT No.: PCT/JP2007/075173
§ 371 (c)(1),
(2), (4) Date: Jun. 24, 2009

(87) PCT Pub. No.: WO2008/081890
PCT Pub. Date: Jul. 10, 2008

(65) Prior Publication Data
US 2010/0063236 A1 Mar. 11, 2010

(30) Foreign Application Priority Data
Dec. 28, 2006 (JP) ................................. 2006-354812

(51) Int. Cl.
*C08G 77/08* (2006.01)
(52) U.S. Cl. ........................................................ 528/21
(58) Field of Classification Search .................... None
See application file for complete search history.

(56) References Cited

U.S. PATENT DOCUMENTS

| 3,503,925 A * | 3/1970 | Griffin ............................. 528/22 |
| 5,302,683 A * | 4/1994 | Weidner et al. ................. 528/21 |
| 5,670,597 A * | 9/1997 | Stepp et al. ..................... 528/21 |
| 2004/0180222 A1 | 9/2004 | Ogihara et al. |
| 2004/0180554 A1 | 9/2004 | Hamada et al. |

FOREIGN PATENT DOCUMENTS

| EP | 0492662 A2 | 7/1992 |
| EP | 1146092 A2 | 10/2001 |
| EP | 1995281 A1 | 11/2008 |
| GB | 2319527 A | 5/1998 |
| JP | 46-21602 A | 6/1971 |
| JP | 47-44040 A | 11/1972 |
| JP | 59176326 A | 10/1984 |
| JP | 61190085 A | 8/1986 |
| JP | 4225031 A | 8/1992 |
| JP | 05043694 A | 2/1993 |
| JP | 10237175 A | 9/1998 |
| JP | 2004-269692 A | 9/2004 |
| JP | 2004-269693 A | 9/2004 |
| JP | 2006-120783 A | 5/2006 |
| JP | 2006-206700 A | 8/2006 |
| JP | 2006-328231 A | 12/2006 |
| JP | 2006-352118 A | 12/2006 |
| JP | 2007-056146 A | 3/2007 |
| JP | 2008-008935 A | 1/2008 |
| TW | 200628573 | 8/2006 |

OTHER PUBLICATIONS

Abstract for JP 46-21602 B (Jun. 1971).*
Abstract for JP 47-44040 B (Nov. 1972).*
English language abstract for JP 59176326 extracted from espacenet.com database dated Oct. 26, 2009, 13 pages, (Oct. 1984).
English language abstract for JP 61190085 extracted from PAJ database, 5 pages, (Aug. 1986).
English language abstract for JP 4225031 extracted from espacenet.com database dated Oct. 26, 2009, 7 pages, (Aug. 1992).
English language translation and abstract for JP 05043694 extracted from PAJ database, 19 pages, (Feb. 1993).
English language translation and abstract for JP 10237175 extracted from PAJ database dated Nov. 2, 2009, 20 pages, (Sep. 1998).
English language translation and abstract for JP 2004-269692 extracted from PAJ database, dated Nov. 2, 2009, 75 pages, (Sep. 2004).
English language translation and abstract for JP 2004-269693 extracted from PAJ database, dated Nov. 2, 2009, 53 pages, (Sep. 2004).
English language translation and abstract for JP 2006-120783 extracted from PAJ database, dated Nov. 2, 2009, 99 pages, (May 2006).
English language translation and abstract for JP 2006-328231 extracted from PAJ database, dated Nov. 2, 2009, 47 pages, (Dec. 2006).
English language translation and abstract for JP 2006-352118 extracted from PAJ database, dated Nov. 2, 2009, 67 pages, (Dec. 2006).
English language translation and abstract for JP 2007-056146 extracted from PAJ database, dated Nov. 3, 2009, 44 pages, (Mar. 2007). English language translation and abstract for JP 2008-008935 extracted from PAJ database, dated Nov. 3, 2009, 74 pages, (Jan. 2008).
English language abstract for JP S46-21602 5 pages, (Jun. 1971).
English language abstract for JP S47-44040 6 pages, (Nov. 1972).
PCT International Search Report for PCT/JP2007/075173, dated Apr. 15, 2008, 4 pages.
English language translation and abstract for JP 2006-206700 extracted from PAJ database, dated Jun. 14, 2010, 51 pages.
European Search Report for Application No. EP 07860395, dated Mar. 12, 2010, 7 pages.

* cited by examiner

*Primary Examiner* — Marc Zimmer
(74) *Attorney, Agent, or Firm* — Howard & Howard Attorneys PLLC

(57) ABSTRACT

In the present invention, when an organopolysiloxane is produced by a dealcoholization condensation reaction between a silicon atom-bonded hydroxy group and a silicon atom-bonded alkoxy group, a quaternary ammonium ion-containing compound such as an alkylammonium hydroxide compound or a silanolate thereof is used as a catalyst. The catalyst for the dealcoholization condensation reaction of the present invention is easily removed after use and is stable. For this reason, when an organopolysiloxane is produced using the aforementioned catalyst, it is not necessary to use complicated production steps or a large amount of the catalyst.

7 Claims, No Drawings

CATALYST FOR DEALCOHOLIZATION CONDENSATION REACTION AND METHOD FOR PRODUCING ORGANOPOLYSILOXANE USING THE SAME

RELATED APPLICATIONS

This application claims priority to and all the advantages of International Patent Application No. PCT/JP2007/075173, filed on Dec. 27, 2007, which claims priority to Japanese Patent Application No. JP2006-354812, filed on Dec. 28, 2006.

TECHNOLOGICAL FIELD

The present application claims priority on the basis of Japanese Patent Application No. 2006-354812, filed in Japan on Dec. 28, 2006, which is hereby incorporated by reference.

The present invention relates to a catalyst for a dealcoholization condensation reaction comprising a quaternary ammonium ion-containing compound, and a method for producing an organopolysiloxane by means of a dealcoholization condensation reaction using the same.

BACKGROUND ART

Conventionally, various basic substances, for example, basic metal salts such as potassium hydroxide, sodium hydroxide, barium hydroxide or the like are used as a catalyst for producing organosilicon compounds such as an organopolysiloxane and the like via a condensation reaction of a silicon atom-bonded hydroxy group, a silicon atom-bonded alkoxy group, or other silicon atom-bonded functional groups.

On the other hand, in Japanese Examined Patent Application, Second Publication No. S46-21602; Japanese Examined Patent Application, Second Publication No. S47-44040; Japanese Unexamined Patent Application, First Publication No. H04-225031; and Japanese Unexamined Patent Application, First Publication No. H05-43694, a tetramethylammonium hydroxide compound is known as a catalyst for obtaining an organopolysiloxane with a high molecular weight by means of ring-opening polymerization of a cyclic siloxane with a low molecular weight such as octamethylcyclotetrasiloxane or the like. Japanese Unexamined Patent Application, First Publication No. 2006-328231 describes that a silsesquioxane derivative having a ladder or random structure is produced by co-hydrolyzing and co-condensing two types of trialkoxysiloxanes, and tetramethylammonium hydroxide is used in the Examples.

In addition, Japanese Unexamined Patent Application, First Publication No. S59-176326 describes a method for making a diorganopolysiloxane with a low molecular weight in which both terminals of the molecular chain thereof are blocked with hydroxy groups have a high molecular weight, in the presence of a filler such as silica or the like using, as a catalyst, a reaction mixture of a quaternary phosphonium hydroxide compound and a diorganosiloxane with a low molecular weight.

[Patent Document 1] Japanese Examined Patent Application, Second Publication No. S46-21602

[Patent Document 2] Japanese Examined Patent Application, Second Publication No. S47-44040

[Patent Document 3] Japanese Unexamined Patent Application, First Publication No. H04-225031

[Patent Document 4] Japanese Unexamined Patent Application, First Publication No. H05-43694

[Patent Document 5] Japanese Unexamined Patent Application, First Publication No. S59-176326

[Patent Document 6] Japanese Unexamined Patent Application, First Publication No. 2006-328231

DISCLOSURE OF THE INVENTION

Problems to be Solved by the Invention

In the case of using a basic metal salt as a catalyst for a condensation reaction, it is necessary to add steps of neutralizing the basic metal salt remaining after completion of the reaction, and removing salts formed thereby by means of filtration or the like. In addition, in order to completely neutralize the basic metal salt, a slightly excess amount of an acidic substance is generally used. In this case, it is necessary to add the step of removing the excess amount of the acidic substance after completion of the neutralization. As described above, the method for producing an organopolysiloxane by means of a condensation reaction with a catalyst of a basic metal salt has problems in that the steps are complicated and waste products are increased.

On the other hand, in the ring-opening polymerization of a cyclic siloxane with a low molecular weight using a tetramethylammonium hydroxide compound as a catalyst, the aforementioned problems in the case of using the basic metal salt can be eluded. However, use of the tetramethylammonium hydroxide compound as a catalyst of a dealcoholization condensation reaction which is completely different from a ring-opening polymerization of a cyclic compound has not been studied heretofore. Tetramethylammonium hydroxide used in the Examples of Japanese Unexamined Patent Application, First Publication No. 2006-328231 is involved in the reaction for dehydration condensation of a silanol obtained by hydrolyzing an alkoxysilane, and is not used as a catalyst for a dealcoholization condensation reaction.

In addition, in the case of making a diorganopolysiloxane with a low molecular weight in which both terminals of the molecular chain thereof are blocked with hydroxy groups have a high molecular weight, using a reaction mixture of a quaternary phosphonium hydroxide compound and a diorganosiloxane with a low molecular weight, as a catalyst, the reaction is a condensation reaction between silicon atom-bonded hydroxy groups. For this reason, the conditions of high temperature and reduced pressure are required, and a large amount of the catalyst must be used. Therefore, the production steps are complicated. In addition, a quaternary phosphonium hydroxide compound remains in the system even after the activity of the compound disappears due to heat, and it is difficult to remove the compound. For this reason, purity of a product is reduced, and the catalyst cannot be used in usage in which high purity is required or usage accompanied with a hydrosilylation reaction since catalyst poisoning is exhibited. Therefore, there are the aforementioned problems.

The present invention is performed under the circumstances of the prior art as described above. An objective of the present invention is to provide a catalyst for a dealcoholization condensation reaction in which it is not necessary to use a large amount of the catalyst, and removal of the catalyst after use is easily carried out, and thereby, establishing a method for producing an organopolysiloxane in which waste products are reduced, and complicated production steps are not necessary.

Means for Solving the Problems

An objective of the present invention can be achieved by using a quaternary ammonium ion-containing compound as a catalyst for a dealcoholization condensation reaction of a silicon atom-bonded hydroxy group and a silicon atom-bonded alkoxy group.

As the aforementioned quaternary ammonium ion-containing compound, an alkylammonium hydroxide compound or a silanolate thereof is preferable. As the aforementioned alkylammonium hydroxide compound, tetramethylammonium hydroxide is preferable. As the aforementioned silanolate of the alkylammonium hydroxide compound, trimethylammonium trimethylsilanolate or a reaction mixture of a tetramethylammonium hydroxide compound and an organopolysiloxane is preferable. In addition, the aforementioned alkylammonium hydroxide compound is preferably in the form of an aqueous solution or an alcohol solution.

The aforementioned catalyst for a dealcoholization condensation reaction is preferably used at the time of subjecting a compound represented by the following average structural formula (I):

$$R^1_a SiO_{[(4-a-b-c)/2]}(OR^2)_b(OH)_c \quad (I)$$

wherein each of $R^1$ and $R^2$ independently represents a monovalent hydrocarbon group;

$0 \leq a < 4$; $0 < b < 4$; $0 < c < 4$; and $c \leq b$, with the proviso that $0 < (a+b+c) < 4$, to a dealcoholization condensation reaction to produce an organopolysiloxane represented by the following average structural formula (II):

$$R^1_a SiO_{[(4-a-b)/2]}(OR^2)_{b-c} \quad (II)$$

wherein $R^1$, $R^2$, a, b and c are the same as described above, with the proviso that $0 < (a+b) < 4$.

The compound represented by the aforementioned average structural formula (I) is preferably obtained by hydrolyzing an alkoxysilane represented by the following general formula (III):

$$R^1_{a'} Si(OR^2)_{b'} \quad (III)$$

wherein $R^1$ and $R^2$ are the same as described above;

a' is 0, 1, 2 or 3; and b' is 1, 2, 3 or 4, with the proviso that (a'+b')=4.

The alkoxysilane represented by the aforementioned average structural formula (III) is preferably selected from the group consisting of tetraalkoxysilane, monoorganotrialkoxysilane, diorganodialkoxysilane, and mixtures thereof.

In addition, the aforementioned catalyst for a dealcoholization condensation reaction is also preferably used when a compound represented by the following average structural formula (IV):

$$R^3_d SiO_{[(4-d-e)/2]}(OR^4)_e \quad (IV)$$

wherein each of $R^3$ and $R^4$ independently represents a monovalent hydrocarbon group; $0 \leq d < 4$ and $0 < e \leq 4$, with the proviso that $0 < (d+e) \leq 4$, and a compound represented by the following average structural formula (V):

$$R^5_f SiO_{[(4-f-g)/2]}(OH)_g \quad (V)$$

wherein $R^5$ represents a monovalent hydrocarbon group; $0 \leq f < 4$ and $0 < g < 4$, with the proviso that $0 < (f+g) < 4$, are subjected to a dealcoholization condensation reaction in a ratio in which the number of moles of the alkoxy groups contained in the compound represented by the aforementioned average structural formula (IV) is equal to or more than the number of moles of the hydroxy groups contained in the compound represented by the average structural formula (V), to produce an organopolysiloxane represented by the following average structural formula (VI):

$$R^3_h R^5_i SiO_{[(4-h-i-j)/2]}(OR^4)_j \quad (VI)$$

wherein $R^3$, $R^4$ and $R^5$ are the same as described above; $0 \leq h < 4$; $0 \leq i < 4$ and $0 \leq j < 4$, with the proviso that $0 < (h+i+j) < 4$.

The aforementioned compound represented by the aforementioned average structural formula (IV) is preferably a tetraalkoxysilane, and the compound represented by the aforementioned average structural formula (V) is preferably a diorganopolysiloxane having silicon atom-bonded hydroxy groups at both terminals of the molecular chain thereof.

Effects of the Invention

The catalyst for a dealcoholization condensation reaction according to the present invention does not require a large amount thereof to be used, and removal thereof after use is easily carried out. Therefore, complication of the after-treatment steps of the dealcoholization condensation reaction can be eluded, and purity of a product can be increased. In addition, increase of waste products can be controlled.

Thereby, a method for producing an organopolysiloxane according to the present invention does not require complicated production steps, and can elude use of a large amount of the catalyst. In addition, the method for producing an organopolysiloxane according to the present invention is not performed via a condensation reaction between hydroxy groups. For this reason, reaction conditions of high temperature and reduced pressure can be alleviated. In view of this, complication of production steps can be eluded.

Therefore, the catalyst for a dealcoholization condensation reaction and the method for producing an organopolysiloxane using the same according to the present invention are practically advantageous, and environmental burden can be reduced.

BEST MODES FOR CARRYING OUT THE INVENTION

The catalyst for a dealcoholization condensation reaction according to the present invention promotes a dealcoholization condensation reaction between a silicon atom-bonded hydroxy group and a silicon atom-bonded alkoxy group, and comprises a quaternary ammonium ion-containing compound. The term "comprise" used herein means not only the case of consisting of only a quaternary ammonium ion-containing compound, but also the case of containing a quaternary ammonium ion-containing compound as the main catalyst component and other additional components.

The quaternary ammonium ion-containing compound is not particularly limited as long as a quaternary ammonium group is possessed. The compound is preferably basic. As examples of a basic compound having a quaternary ammonium ion, mention may be made of an alkylammonium hydroxide compound.

As the alkyl group forming the alkylammonium hydroxide compound, an alkyl group having 1 to 6 carbon atoms is preferable, and examples thereof include a methyl group, an ethyl group, a propyl group, and the like. A reduced number of the carbon atoms is preferable, and in particular, a methyl group is preferable. Therefore, as examples of alkylammonium hydroxide compounds, mention may be made of tetramethylammonium hydroxide, tetraethylammonium hydroxide, tetrapropylammonium hydroxide, tetrabutylammonium hydroxide, and the like. In particular, tetramethylammonium hydroxide is preferable.

A silanolate of an alkylammonium hydroxide compound can also be used as the quaternary ammonium ion-containing compound.

As examples of silanolates of the alkylammonium hydroxide compounds, mention may be made of, for example, tetramethylammonium trimethylsilanolate, tetraethylammonium trimethylsilanolate, tetrapropylammonium trimethylsilanolate, tetramethylammonium triethylsilanolate, tetraethylammonium triethylsilanolate, tetrapropylammonium triethylsilanolate, tetramethylammonium tripropylsilanolate, tetraethylammonium tripropylsilanolate, tetrapropylammonium tripropylsilanolate, and the like. In particular, tetramethylammonium trimethylsilanolate, $\{(CH_3)_4N\text{—}OSi(CH_3)_3\}$, is preferable. As the aforementioned silanolates, those produced by any method can be used. For example, the silanolates can be prepared by a dehydration reaction between a tetraalkylammonium hydroxide compound and a silanol compound.

As a silanolate of an alkylammonium hydroxide compound, a reaction mixture between an alkylammonium hydroxide compound and an organopolysiloxane can also be used. The organopolysiloxane is not particularly limited as long as it can react with the hydroxy group of the alkylammonium hydroxide compound. As examples of organopolysiloxanes, mention may be made of, for example, straight-chain polysiloxanes such as hexamethyldisiloxane, octamethyltrisiloxane, and the like; cyclic siloxanes such as decamethylcyclopentasiloxane, octamethylcyclotetrasiloxane, hexamethylcyclotrisiloxane, and the like; and the like. Preferable examples of the reaction mixture are represented by the following formula:

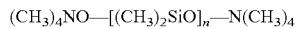

$(CH_3)_4NO\text{—}[(CH_3)_2SiO]_n\text{—}N(CH_3)_4$ wherein n is an integer of one or more.

The catalyst for a dealcoholization condensation reaction according to the present invention may be used as a single type of a quaternary ammonium ion-containing compound, or in combination with two or more types thereof.

In the case of using a tetraalkylammonium hydroxide compound as a quaternary ammonium ion-containing compound, any tetraalkylammonium hydroxide compounds produced by any methods can be used. For example, a tetraalkylammonium hydroxide compound can be produced by means of an electrolysis method in which an aqueous solution of a tetraalkylammonium compound such as tetraalkylammonium halide is supplied to a positive electrode chamber of an electrolytic cell which is distinguished between the positive electrode chamber and a negative electrode chamber by a fluorocarbon-based positive ion exchange membrane, electrolysis is carried out while water is being provided to the aforementioned positive electrode chamber, and subsequently, an aqueous solution of a tetraalkylammonium hydroxide is extracted from the negative electrode chamber, as described in Japanese Unexamined Patent Application, First Publication No. S61-190085.

The aforementioned tetraalkylammonium hydroxide compound is preferably used by diluting in a suitable solvent in view of stability, and is, in particular, in the form of an aqueous solution or an alcohol solution.

In the method for producing an organopolysiloxane of the present invention, an organopolysiloxane is synthesized by means of a dealcoholization condensation reaction between a silicon atom-bonded hydroxy group and a silicon atom-bonded alkoxy group in the presence of a quaternary ammonium ion-containing compound, as a catalyst, which is preferably an alkylammonium hydroxide compound or a silanolate thereof. In the method for producing the organopolysiloxane of the present invention, the organopolysiloxane can be easily produced since the method is performed not via a condensation reaction between silicon atom-bonded hydroxy groups, which requires the conditions of high temperature and reduced pressure.

For example, according to the present invention, a compound represented by the following average structural formula (I):

$R^1_aSiO_{[(4-a-b-c)/2]}(OR^2)_b(OH)_c$    (I)

wherein each of $R^1$ and $R^2$ independently represents a monovalent hydrocarbon group; $0 \leq a < 4$; $0 < b < 4$; $0 < c < 4$; and $c \leq b$, with the proviso that $0 < (a+b+c) < 4$, is subjected to a dealcoholization condensation reaction in the presence of a quaternary ammonium ion-containing compound, and thereby, an organopolysiloxane represented by the following average structural formula (II):

$R^1_aSiO_{[(4-a-b)/2]}(OR^2)_{b-c}$    (II)

wherein $R^1$, $R^2$, a, b and c are the same as described above, with the proviso that $0 < (a+b) < 4$, can be produced. In the aforementioned formula, $c < b$ is preferable.

The aforementioned monovalent hydrocarbon group may be a straight-chain, branched or cyclic hydrocarbon group, having 1 to 30 carbon atoms. As examples of the aforementioned hydrocarbon group, mention may be made of a straight-chain, branched or cyclic alkyl group having 1 to 30 carbon atoms, a straight-chain, branched or cyclic alkenyl group having 2 to 30 carbon atoms, an aryl group having 6 to 30 carbon atoms, an arylalkyl group having 7 to 30 carbon atoms, and the like.

As examples of the aforementioned straight-chain, branched or cyclic alkyl groups, mention may be made of, for example, a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, a neopentyl group, a tert-pentyl group, a cyc-pentyl group, a n-hexyl group, an iso-hexyl group, a sec-hexyl group, a neohexyl group, a cyc-hexyl group, a n-heptyl group, an iso-heptyl group, a sec-heptyl group, a neoheptyl group, a cyc-heptyl group, a n-octyl group, an iso-octyl group, a sec-octyl group, a neooctyl group, a cyc-octyl group, a n-nonyl group, an iso-nonyl group, a sec-nonyl group, a neononyl group, a cyc-nonyl group, a decyl group, an undecyl group, a dodecyl group, a tetradecyl group, a hexadecyl group, and an octadecyl group.

As examples of the aforementioned straight-chain, branched or cyclic alkenyl groups, mention may be made of, for example, a vinyl group, an allyl group, a butenyl group, a hexenyl group, and the like.

As examples of the aforementioned aryl groups, mention may be made of a phenyl group, a tolyl group, a naphthyl group, and the like.

As examples of the aforementioned arylalkyl groups, mention may be made of a phenethyl group, a benzyl group, and the like.

The aforementioned hydrocarbon group may be either substituted or non-substituted. In the case of substituted hydrocarbon groups, as examples of the substituents, mention may be made of, for example, a halogen atom such as a fluorine atom, a chlorine atom, a bromine atom, an iodine atom, or the like; an alkoxy group such as a methoxy group, an ethoxy group, a propoxy group, or the like; a cyano group; and the like. Therefore, as examples of the substituted hydrocarbon groups, mention may be made of, for example, a 3-chloropropyltrimethoxy group, a 3-bromopropyl group, a 3,3,3-trifluoropropyl group, a cyanoethyl group, and the like.

A method for producing an acyclic compound represented by the aforementioned average structural formula (I) is not particularly limited. For example, an alkoxysilane represented by the following general formula (III):

$$R^1_{a'}Si(OR^2)_{b'} \quad (III)$$

wherein $R^1$ and $R^2$ are the same as described above;

a' is 0, 1, 2 or 3; b' is 1, 2, 3 or 4, with the proviso that (a'+b')=4, is hydrolyzed, and thereby, the aforementioned acyclic compound can be obtained. The alkoxysilanes represented by the aforementioned general formula (III) may be used as a single type thereof or as a mixture of two or more types thereof.

As examples of the compounds represented by the aforementioned average structural formula (I), mention may be made of, for example, an organopolysiloxane obtained by hydrolyzing an alkoxysilane of the aforementioned general formula (III) wherein a' and b' are respectively 0 and 4, i.e., a tetraalkoxysilane; an alkoxysilane of the aforementioned general formula (III) wherein a' and b' are respectively 1 and 3, i.e., a monoorganotrialkoxysilane; or a mixture thereof; as well as, an organopolysiloxane obtained by hydrolyzing a mixture produced by adding an alkoxysilane of the aforementioned general formula (III) wherein both a' and b' are 2, i.e., a diorganodialkoxysilane, an alkoxysilane of the aforementioned general formula (III) wherein a' and b' are respectively 3 and 1, i.e., a triorganomonoalkoxysilane, or a mixture thereof to the aforementioned tetraalkoxysilane, the aforementioned monoorganotrialkoxysilane, or a mixture thereof.

As examples of the alkoxysilanes represented by general formula (III), mention may be made of, for example, a tetraalkoxysilane such as tetramethoxysilane, tetraethoxysilane, or the like; a monoorganotrialkoxysilane such as methyltrimethoxysilane, methyltriethoxysilane, methyltripropoxysilane, methyltributoxysilane, ethyltrimethoxysilane, ethyltriethoxysilane, ethyltripropoxysilane, ethyltributoxysilane, propyltrimethoxysilane, propyltriethoxysilane, propyltripropoxysilane, propyltributoxysilane, butyltrimethoxysilane, butyltriethoxysilane, butyltripropoxysilane, butyltributoxysilane, hexyltrimethoxysilane, hexyltriethoxysilane, hexyltripropoxysilane, hexyltributoxysilane, cyclopentyltrimethoxysilane, cyclopentyltriethoxysilane, cyclopentyltripropoxysilane, cyclopentyltributoxysilane, cyclohexyltrimethoxysilane, cyclohexyltriethoxysilane, cyclohexyltripropoxysilane, cyclohexyltributoxysilane, vinyltrimethoxysilane, allyltrimethoxysilane, butenyltrimethoxysilane, hexenyltrimethoxysilane, 3-chloropropyltrimethoxysilane, 3-bromopropyltrimethoxysilane, 3,3,3-trifluoropropyltrimethoxysilane, 2-cyanoethyltrimethoxysilane, phenyltrimethoxysilane, naphthyltrimethoxysilane, phenethylmethoxysilane, or the like; a diorganodialkoxysilane such as dimethyldimethoxysilane, dimethyldiethoxysilane, dimethyldipropoxysilane, dimethyldibutoxysilane, diethyldimethoxysilane, diethyldiethoxysilane, diethyldipropoxysilane, diethyldibutoxysilane, dipropyldimethoxysilane, dipropyldiethoxysilane, dipropyldipropoxysilane, dipropyldibutoxysilane, dibutyldimethoxysilane, dibutyldiethoxysilane, dibutyldipropoxysilane, dibutyldibutoxysilane, dihexyldimethoxysilane, dihexyldiethoxysilane, dihexyldipropoxysilane, dihexyldibutoxysilane, dicyclopentyldimethoxysilane, dicyclopentyldiethoxysilane, dicyclopentyldipropoxysilane, dicyclopentyldibutoxysilane, dicyclohexyldimethoxysilane, dicyclohexyldiethoxysilane or the like; and a triorganomonoalkoxysilane such as trimethylmethoxysilane, trimethylethoxysilane, trimethylpropoxysilane, trimethylbutoxysilane, triethylmethoxysilane, triethylethoxysilane, triethylpropoxysilane, triethylbutoxysilane, tripropylmethoxysilane, tripropylethoxysilane, tripropylpropoxysilane, tripropylbutoxysilane, tributylmethoxysilane, tributylethoxysilane, tributylpropoxysilane, tributylbutoxysilane, trihexylmethoxysilane, trihexylethoxysilane, trihexylpropoxysilane, trihexylbutoxysilane, tricyclopentylmethoxysilane, tricyclopentylethoxysilane, tricyclopentylpropoxysilane, tricyclopentylbutoxysilane, tricyclohexylmethoxysilane, tricyclohexylethoxysilane or the like. It should be understood that the alkoxysilanes represented by the aforementioned general formula (III) are not limited to the aforementioned ones.

In order to promote hydrolysis of the alkoxysilane represented by general formula (III), an acidic or basic catalyst is preferably used. As the acidic catalyst, for example, an inorganic acid such as hydrochloric acid, sulfuric acid or the like, or an organic acid such as acetic acid or the like can be used. As the basic catalyst, an inorganic base such as sodium hydroxide, potassium hydroxide or the like, a basic compound containing a quaternary ammonium ion, and the like can be used. The reaction temperature of the hydrolysis reaction is not particularly limited, and preferably ranges from 20 to 80° C. and more preferably ranges from 30 to 60° C. The reaction pressure of the hydrolysis reaction is not particularly limited, and is preferably a normal pressure in view of operationability.

The compound represented by the aforementioned average structural formula (I) has both a silicon atom-bonded alkoxy group and a silicon atom-bonded hydroxy group per molecule. Therefore, the condensation reaction of the compound represented by the aforementioned average structural formula (I) corresponds to a dealcoholization condensation reaction of the compounds, each compound having both a silicon atom-bonded alkoxy group and a silicone atom-bonded hydroxy group per molecule. The compounds represented by the aforementioned average structural formula (I) may be used as a single type thereof, or as a mixture of two or more types thereof.

In addition, in the present invention, a compound represented by the following average structural formula (IV):

$$R^3_{d}SiO_{[(4-d-e)/2]}(OR^4)_e \quad (IV)$$

wherein each of $R^3$ and $R^4$ independently represents a monovalent hydrocarbon group;

$0 \leq d < 4$ and $0 < e \leq 4$, with the proviso that $0 < (d+e) \leq 4$, and a compound represented by the following average structural formula (V):

$$R^5_{f}SiO_{[(4-f-g)/2]}(OH)_g \quad (V)$$

wherein $R^5$ represents a monovalent hydrocarbon group; $0 \leq f < 4$ and $0 < g < 4$, with the proviso that $0 < (f+g) < 4$, are subjected to a dealcoholization condensation reaction in the presence of a quaternary ammonium ion-containing compound. Thereby, an organopolysiloxane represented by the following average structural formula (VI):

$$R^3_{h}R^5_{i}SiO_{[(4-h-i-j)/2]}(OR^4)_j \quad (VI)$$

wherein

R³, R⁴ and R⁵ are the same as described above; $0 \leq h < 4$; $0 \leq i < 4$ and $0 \leq j < 4$, with the proviso that $0 < (h+i+j) < 4$, can be produced.

The monovalent hydrocarbon group used herein is the same as described in R¹ and R² of the aforementioned average structural formula (I). In the aforementioned formula, $0 < j < 4$ is preferable.

The compound represented by the aforementioned average structural formula (IV) has a silicon atom-bonded alkoxy group, and the compound represented by the aforementioned average structural formula (V) has a silicon atom-bonded hydroxy group. Therefore, the condensation reaction between the compound represented by the aforementioned average structural formula (IV) and the compound represented by the aforementioned average structural formula (V) corresponds to a dealcoholization condensation reaction between the compound having a silicon atom-bonded alkoxy group and the compound having a silicon atom-bonded hydroxy group. When the condensation between the compound of the aforementioned average structural formula (IV) and the compound of the average structural formula (V) is carried out in a ratio in which the number of moles of the alkoxy groups contained in the compound of the aforementioned average structural formula (IV) is equal to or more than the number of moles of the hydroxy groups contained in the compound of the average structural formula (V), and preferably in a ratio in which the number of moles of the alkoxy groups contained in the compound of the aforementioned average structural formula (IV) is equal to or more than twice the number of moles of the hydroxy groups contained in the compound of the average structural formula (V), an organopolysiloxane represented by the aforementioned average structural formula (VI) which substantially contains no hydroxy groups can be obtained. The compounds represented by the aforementioned average structural formula (IV) and the aforementioned average structural formula (V) may be used as a single type thereof or as a mixture of two or more types of each or both thereof. The compounds represented by the aforementioned average structural formula (IV) and the aforementioned average structural formula (V) are silanes or organopolysiloxanes having a straight-chain or branched molecular structure. As examples of the organopolysiloxanes represented by the aforementioned average structural formula (VI), mention may be made of, for example, an organopolysiloxane obtained by means of condensation between a compound of the aforementioned formula (IV) wherein d and e are respectively 0 and 4, i.e., a tetraalkoxysilane; or a compound of the aforementioned formula (IV) wherein d and e are respectively 1 and 3, i.e., a monoorganotrialkoxysilane; and a compound of the aforementioned average structural formula (V) wherein $1.95 \leq (f+g) \leq 2.05$, i.e., a straight-chain or partially branched diorganopolysiloxane.

The usage amount of the catalyst for a dealcoholization condensation reaction formed from the quaternary ammonium ion-containing compound in the method for producing an organopolysiloxane of the present invention may be an amount by which the silicon atom-bonded hydroxy group or the silicon atom-bonded alkoxy group of the starting substances can interact with each other. In general, the catalyst for a dealcoholization condensation reaction is preferably used in an amount ranging from 0.5 to 100,000 ppm, and preferably ranging from 10 to 10,000 ppm, with respect to the weight of the starting materials. If the usage amount thereof is below 0.5 ppm, the rate of the condensation reaction may be extremely reduced. On the other hand, if the usage amount exceeds 100,000 ppm, excessive time may be required in order to remove the catalyst after the condensation reaction.

The dealcoholization condensation reaction in the method for producing an organopolysiloxane of the present invention is preferably carried out at a temperature which is equal to or lower than the thermal decomposition temperature of the catalyst for a dealcoholization condensation reaction comprising the quaternary ammonium ion-containing compound. In general, the aforementioned reaction is carried out at not more than 120° C. and more preferably not more than 100° C., although the thermal decomposition temperature of the aforementioned catalyst varies depending on the types of the aforementioned catalysts.

The reaction pressure of the aforementioned dealcoholization condensation reaction is not particularly limited. Normal pressure is preferably in view of operationability.

In the method for producing an organopolysiloxane of the present invention, after the aforementioned dealcoholization, the remaining catalyst is preferably removed. The removal of the remaining catalyst can be carried out by, for example, heating the aforementioned catalyst to a temperature which is equal to or higher than the thermal decomposition temperature of the quaternary ammonium ion-containing compound which forms the aforementioned catalyst to obtain substances with a low boiling temperature, and subsequently removing the substances from the reaction system by means of an operation under reduced pressure or the like. The heating temperature is, for example, equal to or higher than 120° C., and preferably equal to or higher than 130° C.

For example, tetraalkylammonium hydroxide is thermally decomposed to compounds with a low boiling point such as an amine (such as trimethylamine) and an alcohol (such as methanol) at a temperature which is equal to or higher than the thermal decomposition temperature by means of a reaction shown by the following scheme:

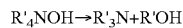

wherein

R' represents an alkyl group such as a methyl group, an ethyl group, a propyl group, or the like.

In addition, the compounds with a low boiling point can be easily removed under reduced pressure. For this reason, the tetraalkylammonium hydroxide remaining in the reaction system can be easily removed. The thermal decomposition reaction of the tetraalkylammonium hydroxide is carried out under reduced pressure and thereby, the removal of the compounds with a low boiling point produced by the thermal decomposition may be promoted, if necessary.

As described above, in the present invention, a neutralization step is not required for removal of the remaining catalyst after the reaction. For this reason, complication of the steps of producing an organopolysiloxane and increase of waste products can be eluded. Therefore, the catalyst for a dealcoholization condensation reaction comprising the quaternary ammonium ion-containing compound in the present invention is practically advantageous.

The organopolysiloxane represented by the aforementioned average structural formula (II) or (VI) which is obtained by the dealcoholization condensation reaction is a straight-chain or branched organopolysiloxane or organosiloxane oligomer, and in general, has a molecular weight ranging from 162 to 1,000,000. In addition, the outer appearance of the organopolysiloxane represented by the aforementioned average structural formula (II) or (VI) may vary in the form of an oil, a gum, or a resin, depending of the molecular weight and molecular structure thereof.

INDUSTRIAL APPLICABILITY

The organopolysiloxane represented by the aforementioned average structural formula (II) or (VI) which is obtained by the method for producing the same of the present invention can be suitably used in various usages.

In particular, when the organopolysiloxane represented by the aforementioned average structural formula (II) or (VI) has an alkoxy group, a reaction such as crosslinking or the like can be carried out by using the aforementioned alkoxy group as a reaction point. Therefore, by use of the organopolysiloxane represented by the aforementioned average structural formula (II) or (VI), a silicone composition can be obtained which is useful as a mono-component type and di-component type curable silicone composition suitable for use in civil engineering and construction; a binder, a surface treatment agent, a sealant, a water repellant, a coating agent for use in electrical insulating, and a painting composition for structural materials as well as various powders suitably used in coating agents; catalyst components for olefin polymerization or the like; a resin modifier composition; or the like.

EXAMPLES

Hereinafter, the present invention is described in detail with reference to Examples. It should be understood that the present invention is not limited to the Examples.

Preparation Example 1

412.8 g (2 mol) of hexyltrimethoxysilane, 20 g of methanol and 0.20 g (0.0020 mol) of concentrated sulfuric acid were placed in a four-neck flask with a volume of 500 ml, equipped with a thermometer, a dripping funnel and a stirring device, and the mixture was stirred. 27.0 g (1.5 mol) of water was added dropwise thereto at room temperature over 20 minutes. The temperature of the reaction mixture was increased by 16° C. by progressing a hydrolysis reaction and a condensation reaction. The reaction mixture after the drop treatment was stirred for 30 minutes at 60° C., and a partial hydrolysis reaction was completed. Subsequently, the reaction mixture was stirred for 10 minutes at 60° C. under reduced pressure of 1 kPa. After methanol produced in the hydrolysis reaction and the condensation reaction was removed, the reaction mixture was cooled to room temperature. As a result, 336.7 g of an organopolysiloxane containing a hexyl group was obtained. The aforementioned partial hydrolysate was used in the following Example 1 and Comparative Example 1.

Example 1

0.70 g (0.002 mol) of a 26% aqueous solution of tetramethylammonium hydroxide was added to 160 g of the organopolysiloxane containing a hexyl group prepared in Preparation Example 1. The mixture was stirred for 30 minutes at room temperature and was stirred for 30 minutes at 60° C., and thereby, a condensation reaction was completed. The reaction mixture exhibited an alkaline property with pH test paper.

The reaction mixture was gradually heated to 100° C. As a result, removal by distillation of methanol produced by the condensation reaction was observed. In addition, the reaction mixture was further heated for one hour at 130° C. As a result, it was confirmed that trimethylamine which was a basic gas produced by thermal decomposition of tetramethylammonium hydroxide used as a catalyst for the condensation reaction generated in a gaseous phase in the flask. The reaction mixture was stirred for 10 minutes at the same temperature as described above under reduced pressure of 1 kPas, and thereby, volatile components were removed. As a result, the mixture exhibited a neutral property with pH test paper.

The aforementioned reaction mixture was filtered under reduced pressure. Thereby, 149.8 g of a neutral organopolysiloxane containing a hexyl group was obtained. The viscosity thereof was 16 mm$^2$/sec. Even after the product was stored for 6 months at room temperature, the viscosity did not change and the product was stable. The average structural formula obtained by means of $^{13}$C NMR was n-C$_6$H$_{13}$SiO$_{0.70}$(OCH$_3$)$_{1.60}$. The number average molecular weight thereof obtained by means of GPC using toluene as a solvent was 375, and the weight average molecular weight was 959.

Comparative Example 1

160 g of the organopolysiloxane containing a hexyl group prepared in Preparation Example 1 and 0.23 g (0.002 mol) of a 48% aqueous solution of potassium hydroxide were placed in a four-neck flask with a volume of 500 ml, equipped with a thermometer, a dripping funnel and a stirring device, and the mixture was stirred for 30 minutes at room temperature, and then was stirred for 30 minutes at 60° C. Thereby, a condensation reaction was completed. The reaction mixture exhibited an alkaline property with pH test paper.

The reaction mixture was gradually heated to 100° C. As a result, removal by distillation of methanol produced by the condensation reaction was observed. In addition, the reaction mixture was further heated for one hour at 130° C., followed by stirring for 30 minutes under reduced pressure of 1 kPas to remove volatile components. The resultant mixture was cooled to room temperature. The reaction mixture exhibited an alkaline property with pH test paper.

Subsequently, in order to neutralize the condensation catalyst, 0.1 g (0.0017 mol) of acetic acid was added thereto. The mixture was stirred for 30 minutes at 100° C., followed by stirring for 30 minutes under reduced pressure of 100 Pas to remove volatile components. Subsequently, the mixture was cooled to room temperature.

The mixture was filtered under reduced pressure. Thereby, 145.6 g of a neutral organopolysiloxane containing a hexyl group was obtained. The viscosity was 17 mm$^2$/sec. Even after the product was stored for 6 months at room temperature, the viscosity thereof did not change and was stable. The average structural formula obtained by means of $^{13}$C NMR was n-C$_6$H$_{13}$SiO$_{0.74}$(OCH$_3$)$_{1.52}$. The number average molecular weight obtained by means of GPC using toluene as a solvent was 408, and the weight average molecular weight was 1062.

Example 2

200 g of a polydimethylsiloxane (average polymerization degree=40) in which both terminals of the molecular chain thereof were blocked with hydroxy groups and 80 g of tetramethoxysilane were placed in a four-neck flask with a volume of 500 ml, equipped with a thermometer, a dripping funnel and a stirring device. In addition, 2.0 g (0.002 mol) of a 26% methanol solution of tetramethylammonium hydroxide was added thereto, followed by mixing. Immediately after mixing, the mixture was a uniform solution which was colorless and transparent. The solution exhibited an alkaline property with pH test paper. As a result of stirring the mixture for 30 minutes at room temperature, the colorless transparent reaction mixture became a clouded mixture. Subsequently, the mixture was stirred for 30 minutes at 60° C. to complete the condensation reaction. The reaction mixture exhibited an alkaline property with pH test paper.

The reaction mixture was gradually heated to 100° C. As a result, removal by distillation of methanol produced by the condensation reaction was observed. In addition, the reaction mixture was further heated for one hour at 130° C. As a result, it was confirmed that trimethylamine which was a basic gas produced by thermal decomposition of tetramethylammonium hydroxide used as a catalyst for the condensation reaction generated in a gaseous phase in the flask. The reaction mixture was stirred for 10 minutes at the same temperature as described above under reduced pressure of 1 kPas, and thereby, volatile components were removed. As a result, the mixture exhibited a neutral property with pH test paper.

The aforementioned reaction mixture was filtered under reduced pressure. Thereby, 149.8 g of a neutral polydimethylsiloxane in which both the terminals of the molecular chain thereof were blocked by trimethoxysilyl groups was obtained. The viscosity thereof was 127 mm$^2$/sec. The average structural formula obtained by means of $^{13}$C NMR was $(CH_3)_{1.91}SiO_{0.98}(OCH_3)_{0.14}$. The number average molecular weight thereof obtained by means of GPC using toluene as a solvent was $4.7\times10^3$, and the weight average molecular weight was $9.8\times10^3$. From $^{29}$Si NMR analysis, it was confirmed that the hydroxy groups at the terminals of the molecular chain did not remain.

The invention claimed is:

1. A method for producing an organopolysiloxane represented by the following average structural formula (II), characterized by subjecting a compound represented by the following average structural formula (I):

   (I)

wherein each of $R^1$ and $R^2$ independently represents a monovalent hydrocarbon group; $0\leq a<4$; $0<b<4$; $0<c<4$; and $c\leq b$, with the proviso that $0<(a+b+c)<4$,
to a dealcoholization condensation reaction in the presence of a quaternary ammonium ion-containing catalyst to produce the organopolysiloxane represented by the following average structural formula (II):

   (II)

wherein $R^1$, $R^2$, a, b and c are the same as described above, with the proviso that $0<(a+b-c)<4$, and wherein the compound represented by said average structural formula (I) is obtained by hydrolyzing an alkoxysilane in the presence of an acid or a base, wherein the alkoxy silane is represented by the following general formula (III):

   (III)

wherein $R^1$ and $R^2$ are the same as described above;
a' is 0, 1, 2 or 3; and b' is 1, 2, 3 or 4, with the proviso that (a'+b')=4, with the proviso that the alkoxy silane is not hydrolyzed in the presence of a quaternary ammonium ion-containing catalyst.

2. The method according to claim 1, wherein the alkoxysilane represented by said average structural formula (III) is an alkoxysilane selected from the group consisting of a tetraalkoxysilane, monoorganotrialkoxysilane, diorganodialkoxysilane, and a mixture thereof.

3. The method according to claim 1, wherein said quaternary ammonium ion-containing compound is an alkylammonium hydroxide compound or a silanolate thereof.

4. The method according to claim 3, wherein the silanolate of said alkylammonium hydroxide compound is tetramethylammonium trimethylsilanolate or a reaction product of a tetramethylammonium hydroxide compound and an organopolysiloxane.

5. A method for producing an organopolysiloxane represented by the following average structural formula (VI), characterized by subjecting a compound represented by the following average structural formula (IV):

   (IV)

wherein each of $R^3$ and $R^4$ independently represents a monovalent hydrocarbon group; $0\leq d<4$ and $0<e\leq 4$, with the proviso that $0<(d+e)\leq 4$,
and a compound represented by the following average structural formula (V):

   (V)

wherein $R^5$ represents a monovalent hydrocarbon group; $0\leq f<4$ and $0<g<4$, with the proviso that $0<(f+g)<4$, to a dealcoholization condensation reaction in the presence of a quaternary ammonium ion-containing catalyst in a ratio in which the number of moles of the alkoxy group contained in the compound represented by the following average structural formula (IV) is equal to or more than the number of moles of the hydroxy group contained in the compound represented by the average structural formula (V), to produce said organopolysiloxane represented by the following average structural formula (VI):

   (VI)

wherein $R^3$, $R^4$ and $R^5$ are the same as described above; $0\leq h<4$; $0\leq i<4$ and $0\leq j<4$, with the proviso that $0<(h+i+j)<4$, wherein said quaternary ammonium ion-containing catalyst is an alkylammonium hydroxide compound or a silanolate thereof.

6. The method according to claim 5, wherein the compound represented by said average structural formula (IV) is a tetraalkoxysilane, and the compound represented by said average structural formula (V) is a diorganopolysiloxane having silicon atom-bonded hydroxy groups at both terminals of the molecular chain thereof.

7. The method according to claim 5, wherein the silanolate of said alkylammonium hydroxide compound is tetramethyl ammonium trimethylsilanolate or a reaction product of a tetramethylammonium hydroxide compound and an organopolysiloxane.

* * * * *